United States Patent [19]

Barnes et al.

[11] Patent Number: 4,695,455
[45] Date of Patent: * Sep. 22, 1987

[54] CELLULAR ENCAPSULATION OF PESTICIDES PRODUCED BY EXPRESSION OF HETEROLOGOUS GENES

[75] Inventors: Andrew C. Barnes, San Diego; Susan G. Cummings, Chula Vista, both of Calif.

[73] Assignee: Mycogen Corporation, San Diego, Calif.

[*] Notice: The portion of the term of this patent subsequent to Sep. 22, 2004 has been disclaimed.

[21] Appl. No.: 771,313

[22] Filed: Aug. 30, 1985

Related U.S. Application Data

[63] Continuation-in-part of Ser. No. 693,080, Jan. 22, 1985, abandoned.

[51] Int. Cl.[4] ..................... A01N 63/00; C12P 21/00; C12N 15/00; C12N 1/20
[52] U.S. Cl. ........................................ 424/93; 435/68; 435/172.3; 435/253; 435/254; 435/317; 435/255; 435/260; 47/58
[58] Field of Search ................. 435/68, 172.3, 31, 32, 435/317, 253, 243, 257, 260, 261; 47/58; 424/93, 88, 92

[56] References Cited

U.S. PATENT DOCUMENTS

| | | | |
|---|---|---|---|
| 3,779,869 | 12/1973 | Zienty .................................. | 195/68 |
| 4,000,258 | 12/1976 | Shieh et al. ........................... | 424/93 |
| 4,265,880 | 5/1981 | Spence et al. ......................... | 424/93 |
| 4,328,203 | 5/1982 | Spence et al. ......................... | 424/16 |
| 4,337,313 | 6/1982 | Hershberger et al. ............... | 435/177 |
| 4,374,200 | 2/1983 | Olsen .................................. | 435/172 |
| 4,609,550 | 9/1986 | Fitz-James .......................... | 424/93 |

FOREIGN PATENT DOCUMENTS

| 51-5047 | 7/1981 | Japan .................................... | 424/93 |
|---|---|---|---|

OTHER PUBLICATIONS

Schnepf et al., *Proc. Natl. Acad. Sci.*, vol. 78 (5) May 1981, "Cloning and Expression of the *Bacillus thuringiensis* Crystal Protein in *Eschenchia coli*", pp. 2893–2897.
Ohgaki et al, *Chem Abst*, vol. 83, 1975, No. 2287m, "Synergistic Antimicrobial Action of Formalin".
Gotterdi et al, *Chem Abst*, vol. 193, No. 80030t, 1980, "Redox Potential and Germicidal Action of Aqueous Halogen Solutions".
Ward et al, *FEBS*, Oct. 1984, vol. 175(2), pp. 377–382, "Cloning and Expression in *Eschenchia coli* of the Insecticidal γ-Endotoxin Gene of *Bacillus thuringiensis*, var. Israelensis".
Hawkes *Electron Optics and Electron Microscopy*, 1972, Taylor & Francis Ltd, pp. 214–215.
Wischitzer, *Introduction to Electron Microscopy*, pp. 125–135, Prergamon Press 1982.
Glauert, Audrey from *Techniques for Electron Microscopy*, 1961.
Fawcett, Don W., from *Modern Developments in Electron Microscopy*, 1964.

*Primary Examiner*—Thomas G. Wiseman
*Assistant Examiner*—Robin Lyn Teskin
*Attorney, Agent, or Firm*—Roman Saliwanchik; David R. Saliwanchik

[57] ABSTRACT

Methods and compositions are provided for preparing and using pesticides, where the pesticides are encapsulated in non-proliferating cells. The methods involve introducing a heterologous gene into a cellular host, where expression of the heterologous gene results, directly or indirectly, in production of the pesticide. These cells are then killed under conditions which prolong the pesticidal activity when said cells are applied to the environment of a target pest. The killed cells can be used directly or after formulation for treatment of an agricultural host or environment of the host with the pesticide.

19 Claims, No Drawings

CELLULAR ENCAPSULATION OF PESTICIDES PRODUCED BY EXPRESSION OF HETEROLOGOUS GENES

CROSS REFERENCE TO A RELATED APPLICATION

This is a continuation-in-part of our copending application Ser. No. 693,080, now abandoned filed on Jan. 22, 1985.

BACKGROUND OF THE INVENTION

The extraordinary increase in agricultural productivity has been a result of many factors, including significantly better understanding of the methods involved with agriculture, improved equipment, availability of fertilizers, and improved pesticides. The latter factor has not been without detrimental aspects, however, due to the negative effect on the environment. There is, therefore, a substantial interest in developing effective and environmentally acceptable pesticides.

Among ecologically acceptable pesticides are the protein toxins produced by various microorganisms, such as *Bacillus thuringiensis*. However, the use of *B. thuringiensis* lysate or spores as a pesticide has significant drawbacks. The lifetime of the pesticide is relatively short in the environment, requiring multiple applications to give adequate protection. Consequently, these pesticides are not economical in comparison to more traditional chemical products having long residual activities. Improvements in field longevity would greatly aid in expanding the application of biological, or protein toxin-based pesticides.

As indicated above, there are many requirements for pesticides associated with their particular application. For example, in many cases it is desirable to have pesticides which have long residual activity in the field while not accumulating in the environment. In addition, because of economic considerations, it is preferable to have pesticides which have a reasonably broad spectrum of biocidal activity. Also, the pesticide should degrade to degradation products which are environmentally acceptable. Other considerations include ease of formulation, pesticidal activity, stability to environmental effects, such as light, water, organisms, and the like, and effect on beneficial or innocuous organisms in the environment.

U.S. Pat. No. 4,265,880 describes embedding live insecticidal pathogens in a coacervate microbead. Japanese Pat. No. 51-5047 describes physical-chemical methods for killing B.t. spores, while retaining toxicity.

BRIEF SUMMARY OF THE INVENTION

Methods and compositions are provided for protecting agricultural crops and products from pests. The pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. This naturally encapsulated pesticide may then be formulated in accordance with conventional techniques for application to the environment hosting a target pest, e.g., soil, water, and foliage of plants.

DETAILED DISCLOSURE OF THE INVENTION

In accordance with the subject invention, improved pesticides are provided, having among their other advantages an extended residual life, by modifying pesticide producing microorganisms hosting a heterologous gene capable of expression in the host, where expression of the gene results, directly or indirectly, in the production of a pesticide. The subject method involves treating the organisms with reagents that prolong the activity of the toxin produced in the cell when the cell is applied to the environment of target pest(s). The resulting product retains the toxicity of the toxin.

A wide variety of pesticides can be produced which will be characterized by being capable of being produced intracellularly, particularly in a unicellular microorganism host, such as prokaryotes, e.g., bacteria: or eukaryotes, e.g., fungi, exemplified by yeast and filamentous fungi, such as Neurospora and Aspergillus: or protists, such as amoebas, protozoa, algae, and the like.

The pesticide can be any toxin produced by a microbe. For example, it can be a polypeptide which has toxic activity toward a eukaryotic multicellular pest, such as insects, e.g., coleoptera, lepidoptera, diptera, hemiptera, dermaptera, and orthoptera: or arachnids: gastropods: or worms, such as nematodes and platyhelminths. Various susceptible insects include beetles, moths, flies, grasshoppers, lice, and earwigs.

The pesticide which is produced in the host cell may be a polypeptide produced in active form or a precursor or proform which requires further processing for toxin activity, e.g., by the pest, as with the crystal toxin of *B. thuringiensis* var. *kurstaki*. Thus, the gene may encode an enzyme which modifies a metabolite to produce a pesticidal composition.

Among naturally-occurring toxins are the polypeptide crystal toxins of *B. thuringiensis* var. *kurstaki*, active against lepidoptera; *B.t.* var. *israelensis*, active against mosquitoes: *B.t.* M-7, active against coleoptera: *B. thuringiensis* var. *aizawai*, active against spodoptera: and *B. sphaericus*, active against mosquito larvae. Other toxins include those of entomopathogenic fungi, such as beauverin of *Beauveria bassiana* and destruxins of *Metarhizium* spp.; or the broad spectrum insecticidal compounds, such as the avermectins of *Streptomyces avermitilus*. Cultures exemplifying the above are as follows:

*Baccillus thuringiensis* var. *kurstaki* HD—1—NRRL B-3792 disclosed in U.S. Pat. 4,448,885

*Bacillus thuringiensis* var. *israelensis*—ATCC 35646

*Bacillus thuringiensis* M—7—NRRL B-15939

The following *B. thuringiensis* cultures are available from the U.S. Department of Agriculture (USDA) at Brownsville, Tex. Requests should be made to Joe Garcia, USDA, ARS, Cotton Insects Research Unit, P.O. Box 1033, Brownsville, Tex. 78520 USA.

*B. thuringiensis* HD2
*B. thuringiensis* var. *finitimus* HD3
*B. thuringiensis* var. *alesti* HD4
*B. thuringiensis* var. *kurstaki* HD73
*B. thuringiensis* var. *sotto* HD770
*B. thuringiensis* var. *dendrolimus* HD7
*B. thuringiensis* var. *kenyae* HD5
*B. thuringiensis* var. *galleriae* HD29
*B. thuringiensis* var. *canadensis* HD224
*B. thuringiensis* var. *entomocidus* HD9
*B. thuringiensis* var. *subtoxicus* HD109
*B. thuringiensis* var. *aizawai* HD11
*B. thuringiensis* var. *morrisoni* HD12

*B. thuringiensis* var. *ostriniae* HD501
*B. thuringiensis* var. *tolworthi* HD537
*B. thuringiensis* var. *darmstadiensis* HD146
*B. thuringiensis* var. *toumanoffi* HD201
*B. thuringiensis* var. *kyushuensis* HD541
*B. thuringiensis* var. *thompsoni* HD542
*B. thuringiensis* var. *pakistani* HD395
*B. thuringiensis* var. *israelensis* HD567
*B. thuringiensis* var. *indiana* HD521
*B. thuringiensis* var. *dakota*
*B. thuringiensis* var. *tohokuensis* HD866
*B. thuringiensis* var. *kumanotoensis* HD867
*B. thuringiensis* var. *tochigiensis* HD868
*B. thuringiensis* var. *colmeri* HD847
*B. thuringiensis* var. *wuhanensis* HD525
*Bacillus cereus*—ATCC 21281
*Bacillus moritai*—ATCC 21282
*Bacillus popilliae*—ATCC 14706
*Bacillus lentimorbus*—ATCC 14707
*Bacillus sphaericus*—ATCC 33203
*Beauveria bassiana*—ATCC 9835
*Metarhizium anisopliae*—ATCC 24398
*Metarhizium flavoviride*—ATCC 32969
*Streptomyces avermitilus*—ATCC 31267

The toxin need not be the same as a naturally occurring toxin. Polypeptide toxins may be fragments of a naturally-occurring toxin; expression products of deletion, transversion or transition mutations, where two or fewer number percent of the amino acids may be changed; or a repetitive sequence capable of processing by the intended pest host. In addition, fusion products may be prepared where one, five or more amino acids are provided at the N-terminus to provide, for example, reduced proteolytic degradation of the toxin(s). In some instances, a plurality of the same or different toxins may be encoded and expressed, where processing sites may be introduced between each toxin moiety in the polytoxin.

Illustrative host cells may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiaceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the heterologous gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity: lack of mammalian toxicity attractiveness to pests for ingestion; ease of killing and fixing without damage to the toxin and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such Pseudomonas sp., Erwinia sp. and Flavobacterium sp.; or such other organisms as Escherichia, Lactobacillus sp., Bacillus sp., and the like. Specific organisms include *Pseudomonas aeruginosa*, *Pseudomonas fluorescens*, *Saccharomyces cerevisiae*, *Bacillus thuringiensis*, *Escherichia coli*, *Bacillus subtilis*, and the like.

The cell will usually be intact and be substantially in the proliferative form when killed, rather than in a spore form, although in some instances spores may be employed.

The cells may be inhibited from proliferation in a variety of ways, so long as the technique does not deleteriously affect the properties of the pesticide, nor diminish the cellular capability in protecting the pesticide. The techniques may involve physical treatment, chemical treatment, changing the physical character of the cell or leaving the physical character of the cell substantially intact, or the like.

Various techniques for inactivating the host cells include heat, usually 50° C. to 70° C.; freezing; UV irradiation; lyophilization; toxins, e.g., antibiotics; phenols; anilides, e.g., carbanilide and salicylanilide; hydroxyurea; quaternaries alcohols; antibacterial dyes; EDTA and amidines non-specific organic and inorganic chemicals, such as halogenating agents, e.g., chlorinating, brominating or iodinating agents; aldehydes, e.g., glutaraldehyde or formaldehyde; toxic gases, such as ozone and ethylene oxide peroxide; psoralens; desiccating agents; or the like, which may be used individually or in combination. The choice of agent will depend upon the particular pesticide, the nature of the host cell, the nature of the modification of the cellular structure, such as fixing and preserving the cell wall with cross-linking agents, or the like.

The cells generally will have enhanced structural stability which will enhance resistance to environmental degradation in the field. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bioavailability or bioactivity of the toxin.

The heterologous gene(s) may be introduced into the host in any convenient manner, either providing for extrachromosomal maintenance or integration into the host genome. (By heterologous is intended that the gene is not present in the host into which it is introduced, nor would the gene normally be found in such host. That is, even if the host organism and the source of the heterologous gene exchange information, the heterologous gene would normally not be found in the wild-type host cells in nature. Usually, the term heterologous will involve species of different genera as host and gene source.)

Various constructs may be used, which include replication systems from plasmids, viruses, or centromeres in combination with an autonomous replicating segment (ars) for stable maintenance. Where only integration is desired, constructs can be used which may provide for replication, and are either transposons or have transposon-like insertion activity or provide for homology with the genome of the host. Frequently, DNA sequences are employed having the heterologous gene between sequences which are homologous with sequences in the genome of the host, either chromosomal or plasmid. Desirably, the heterologous gene(s) will be present in multiple copies. See for example, U.S. Pat. No. 4,399,216. Thus, conjugation, transduction, transfection and transformation may be employed for introduction of the heterologous gene.

A large number of vectors are presently available which depend upon eukaryotic and prokaryotic replication systems, such as ColE1, P-1 incompatibility plasmids, e.g., pRK290, yeast 2m $\mu$ plasmid, lambda, and the like.

Where an extrachromosomal element is employed, the DNA construct will desirably include a marker which allows for a selection of those host cells containing the construct. The marker is commonly one which provides for biocide resistance, e.g., antibiotic resistance or heavy metal resistance, complementation providing prototrophy to an auxotrophic host, or the like. The replication systems can provide special properties, such as runaway replication, can involve cos cells, or other special feature.

Where the heterologous gene(s) has transcriptional and translational initiation and termination regulatory signals recognized by the host cell, it will frequently be satisfactory to employ those regulatory features in conjunction with the heterologous gene. However, in those situations where the heterologous gene is modified, as for example, removing a leader sequence or providing a sequence which codes for the mature form of the pesticide, where the entire gene encodes for a precursor, it will frequently be necessary to manipulate the DNA sequence, so that a transcriptional initiation regulatory sequence may be provided which is different from the natural one.

A wide variety of transcriptional initiation sequences exist for a wide variety of hosts. The sequence can provide for constitutive expression of the pesticide or regulated expression, where the regulation may be inducible by a chemical, e.g., a metabolite, by temperature, or by a regulatable repressor. See for example, U.S. Pat. No. 4,374,927. The particular choice of the promoter will depend on a number of factors, the strength of the promoter, the interference of the promoter with the viability of the cells, the effect of regulatory mechanisms endogenous to the cell on the promoter, and the like. A large number of promoters are available from a variety of sources, including commercial sources.

The cellular host containing the heterologous pesticidal gene may be grown in any convenient nutrient medium, where the DNA construct provides a selective advantage, providing for a selective medium so that substantially all or all of the cells retain the heterologous gene. These cells may then be harvested in accordance with conventional ways and modified in the various manners described above. Alternatively, the cells can be fixed prior to harvesting.

The method of treating the host organism containing the toxin can fulfill a number of functions. First, it may enhance structural integrity. Second, it may provide for enhanced proteolytic stability of the toxin, by modifying the toxin so as to reduce its susceptibility to proteolytic degradation and/or by reducing the proteolytic activity of proteases naturally present in the cell. The cells are preferably modified at an intact stage and when there has been a substantial build-up of the toxin protein. These modifications can be achieved in a variety of ways, such as by using chemical reagents having a broad spectrum of chemical reactivity. The intact cells can be combined with a liquid reagent medium containing the chemical reagents, with or without agitation at temperatures in the range of about $-10°$ to $60°$ C. The reaction time may be determined empirically and will vary widely with the reagents and reaction conditions. Cell concentrations will vary from about $10E^2$ to $10E^{10}$ per ml.

Of particular interest as chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde anti-infectives, such as zephiran chloride and cetylpyridinium chloride alcohols, such as isopropyl and ethanol various histologic fixatives, such as Bouin's fixative and Helly's fixative (See: Humason, Gretchen L., Animal Tissue Techniques, W. H. Freeman and Company, 1967); or a combination of physical (heat) and chemical agents that prolong the activity of the toxin produced in the cell when the cell is applied to the environment of the target pest(s).

For halogenation with iodine, temperatures will generally range from about 0° to 50° C., but the reaction can be conveniently carried out at room temperature. Conveniently, the iodination may be performed using triiodide or iodine at 0.5 to 5% in an acidic aqueous medium, particularly an aqueous carboxylic acid solution that may vary from about 0.5–5M. Conveniently, acetic acid may be used, although other carboxylic acids, generally of from about 1 to 4 carbon atoms, may also be employed. The time for the reaction will generally range from less than a minute to about 24 hrs, usually from about 1 to 6 hrs. Any residual iodine may be removed by reaction with a reducing agent, such as dithionite, sodium thiosulfate, or other reducing agent compatible with ultimate usage in the field. In addition, the modified cells may be subjected to further treatment, such as washing to remove all of the reaction medium, isolation in dry form, and formulation with typical stickers, spreaders, and adjuvants generally utilized in agricultural applications, as is well known to those skilled in the art.

Of particular interest are reagents capable of crosslinking the cell wall. A number of reagents are known in the art for this purpose. The treatment should result in enhanced stability of the pesticide. That is, there should be enhanced persistence or residual activity of the pesticide under field conditions. Thus, under conditions where the pesticidal activity of untreated cells diminishes, the activity of treated cells remains for periods of from 1 to 3 times longer.

The cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about 1E2 to about 1E4 cells/mg. These formulations will be administered at about 2 oz (liquid or dry) to 2 or more lb/ha.

The formulations can be applied to the environment of the pest(s), e.g., plants, soil or water, by spraying, dusting, sprinkling or the like.

The following examples are offered by way of illustration and not by way of limitation.

EXAMPLE 1 CONSTRUCTION OF A HETEROLOGOUS GENE AND TRANSFORMATION INTO A SUITABLE HOST

A construction began with a clone of *Pseudomonas aeruginosa*, available from Northern Regional Research Laboratories (NRRL B-12127), containing a broad host range shuttle plasmid pRO1614 (J. Bact. [1982]150:60: U.S. Pat. No. 4,374,200). The plasmid has unique HindIII, BamHI, and SalI and PvuII restriction sites, a PstI insertion, which includes the carbenicillin resistance gene and a *P. aeruginosa* replication system, where the HindIII, BamHi and SalI restriction sites are in a tetracycline resistance gene. The remainder of the plasmid is derived from pBR322. A second plasmid, pSM-117, has been deposited as a clone of *E. coli* (NRRL B-15976). This deposit was made with the permanent collection of the Northern Regional Research Laboratory, U.S. Department of Agriculture, Peoria, Ill. 61604, USA. Plasmid pSM-117 confers ampicillin resistance to *E. coli* and contains a 6.8 Kbp HindIII DNA fragment that includes the δ-endotoxin gene from the 50 md plasmid of *Bacillus thuringiensis* HD73. Sufficient toxin is expressed from this gene in *E. coli* to make the intact cells toxic to cabbage loopers. A further modification of the DNA fragment was done to enhance toxin expression and to accomplish expression of toxin in an alternate host, *Pseudomonas fluorescens.* In order to eliminate unwanted DNA from the 6.8 Kbp fragment, pSM-117 was digested with BamHl to open the circular plasmid at a site nearest to the 5′ end of the toxin gene, and was treated with the exonuclease Bal31 to reduce the 6.8 Kbp HindII insert to about 2.9 Kbp. The free ends of the DNA were filled in with Klenow polymerase, BamHl linkers were added, and the linear DNA was ligated to reform the circular plasmid. The resultant vector, pFG270, was digested with XhoI to open the circular plasmid at a site nearest to the 3′ end of the toxin gene. SalI linkers were added, the plasmid was ligated to its circular form, and the resultant vector, pFG10.6 was amplified in *E. coli.* pFG10.6 was digested completely with SalI and BamHI and the resulting 2.1 Kbp fragment containing the toxin gene was purified by gel electrophoresis and ligated into the BamHI and SalI sites of plasmid pRO1614. The resultant plasmid, pCH2.1, was amplified in *E. coli* and used to transform *Pseudomonas fluorescens* to carbenicillin resistance and the ability to synthesize δ-endotoxin. *Pseudomonas fluorescens* (pCH2.1) was deposited with NRRL and was given the accession number NRRL B-15977. In the following illustrative experiments *P. fluorescens* (pCH2.1) was used in conjunction with controls of untransformed cells.

The culture deposits *E. coli* (pSM-117)--NRRL B-15976 and *P. fluorescens* (pCH2.1)--NRRL B-15977 were made in the permanent collection of the NRRL repository, to be maintained for at least thirty years. These deposits are available to the public upon the grant of a patent disclosing them. The deposits are also available as required by foreign patent laws in countries wherein counterparts of the subject application, or its progeny, are filed. However, it should be understood that the availability of a deposit does not constitute a license to practice the subject invention in derogation of patent rights granted by governmental action.

EXAMPLE 2 TREATMENT AND TESTING OF MICROBES HOSTING A HETEROLOGOUS GENE

The Pseudomonads were either killed by 1% lugol's iodine (100 g KI, 50 g $I_2$, 100 ml glacial acetic acid in 1 L sterile distilled water) or by treatment with a 2% formalin solution, each at ambient temperatures.

Cell pellets from two liter broth cultures of *P. fluorescens* with and without *B.t.* toxin are divided in half. Half the cells are treated with 1% lugol's iodine for 4 hr, while the other half are held on ice. Washed lugol's treated cells and untreated cells are repelleted in 10 ml of sterile deionized water. Nine ml of this suspension (10E8-10E12 cells/ml) are sprayed on three young lettuce plants. The three sprayed plants are placed in a single enclosed chamber and 50-75 *Trichoplusia ni* larvae are applied to the plants. Plants are considered protected if there is no visible loss of foliage over the observation period.

TABLE 1

| | Plant Assay 1 - *P. fluorescens* | | | |
|---|---|---|---|---|
| Microorganism | Treatment | # Viable Cells/ml | Total # Larvae | Protection |
| *P. fluorescens* | Live | 2.5 × 10E11 | 75 | Not protected |
| *P. fluorescens* + Bt Toxin | Live | 3.1 × 10E11 | 75 | Protected |
| *P. fluorescens* | 1% Lugol's Iodine 4 hrs | 0 | 75 | Not protected |
| *P. fluorescens* + Bt Toxin | 1% Lugol's Iodine 4 hrs | 0 | 75 | Protected |

*Set up day 1, 25 2-day larvae applied to plants, day 3, 50 5-day larvae applied to plants, day 10, observation reported.

In the next study, newly hatched cabbage loopers are placed in a Petri dish containing droplets of the material to be bioassayed. The larvae imbibe the liquid and are then removed to small cups containing larval diet. The larvae are examined after seven days and the total number of animals killed is recorded. The following Table 2 indicates the results.

TABLE 2

| Microorganism | Treatment | # Larvae Killed/ Total | % Larvae Killed | Viable Cell Count/ ml |
|---|---|---|---|---|
| Bioassay 1 - P. fluorescens | | | | |
| P. fluorescens | Live | 0/15 | 0 | 8 × 10E11 |
| P. fluorescens + Bt Toxin | Live | 11/18 | 62 | 2.5 × 10E12 |
| P. fluorescens | 1% Lugol's 4 hrs | 0/15 | 0 | 0 |
| P. fluorescens + Bt Toxin | 1% Lugol's 4 hrs | 8/13 | 62 | 0 |
| Bioassay 2 - P. fluorescens | | | | |
| P. fluorescens | Live | 0/15 | 0 | 3.7 × 10E11 |
| P. fluorescens + Bt Toxin | Live | 3/20 | 15 | 4.5 × 10E11 |
| P. fluorescens | 1% Lugol's 4 hrs | 0/15 | 0 | 0 |
| P. fluorescens + Bt Toxin | 1% Lugol's 4 hrs | 8/15 | 53 | 0 |
| Bioassay 3 - P. fluorescens | | | | |
| P. fluorescens + Bt Toxin | Live-frozen 14 days | 9/10 | 90 | 2.5 × 10E12 |
| P. fluorescens | 1% Lugol's 4 hrs | 1/15 | 7 | 0 |
| P. fluorescens + Bt Toxin | 1% Lugol's 4 hrs | 11/15 | 73 | 0 |
| P. fluorescens | 2% formalin 4 hrs | 0/15 | 0 | 0 |
| P. fluorescens + Bt Toxin | 2% formalin 4 hrs | 10/15 | 67 | 0 |
| Bioassay 4 - P. fluorescens | | | | |
| P. fluorescens | Live | 6/14 | 30 | 3 × 10E11 |
| P. fluorescens + Bt Toxin | Live | 20/20 | 100 | 3 × 10E10 |
| P. fluorescens | 1% Lugol's 4 hrs | 0/20 | 0 | 0 |
| P. fluorescens + Bt Toxin | 1% Lugol's 4 hrs | 18/20 | 90 | 0 |

In the next study, different methods of killing the cells were employed to determine the effect on cell stability to sonication. *P. fluorescens* strain 33 is an untransformed cell not containing the Bt toxin, while strain pCH contains the 2.1 kb toxin gene. In the first study, stationary phase cultures of strain 33 and strain pCH were harvested by centrifugation and cell pellets suspended in sterile deionized water at concentrations of 10E10 and 10E9, respectively. Aliquots of cells were exposed to a 70° C. water bath for varying amounts of time and cell viability measured by plate counts on King's B agar. (See King, E. O. et al.(1954) J. Lab. & Clin. Med. 44:304. The medium has the following ingredients: Proteose peptone No. 3, 2.0 percent; Bacto agar, 1.5 percent; glycerol, C.P., 1.0 percent $K_2HPO_4$ [anhydrous], 0.15 percent: $MgSO_4 \cdot 7H_2O$, 0.15 percent; adjusted to pH 7.2.) Strain 33 was substantially completely killed within 5 min, while strain pCH showed substantially no viable cells within 10 min.

Cells of strain 33 (untreated, heat treated at 70° C., or lugol's treated [1% lugol's iodine, 2 hr, room temperature]) were suspended in 10 ml deionized water to give a cell concentration of approximately 10E9/ml. The cell suspension was then subjected to sonication for 5 min on a Bronson 200 Sonifier (using a microprobe output 10, 50% duty cycle, pulse mode). The optical density (575 nm) of the cell suspension was measured before and after the sonication treatment. A decrease in optical density indicates cell disruption. The following Tables 3 and 4 give the results.

TABLE 3

| Sonication - *P. fluorescens* 33 | | |
|---|---|---|
| | Optical Density (575 nm) | |
| Treatment | Pre-sonication | Post-sonication |
| Live | 0.24 | 0.05 |
| Lugol's (1%, 2 hr, room temp) | 0.20 | 0.19 |
| Heat 70° C. | | |
| 1 | 0.22 | 0.06 |
| 3 | 0.21 | 0.07 |
| 5 | 0.22 | 0.09 |
| 15 | 0.20 | 0.10 |
| 30 | 0.21 | 0.11 |
| 60 | 0.19 | 0.13 |
| 90 | 0.22 | 0.13 |

Cells of strain pCH (5×10E10/ml) were heat treated in a 70° C. water bath and assayed for toxicity against *T. ni* larvae. The bioassay procedure involved newly hatched cabbage loopers which were placed in a petri dish containing droplets of the materials to be bioassayed. The larvae were allowed to imbibe the liquid and were then removed to small cups containing larval diet. The larvae were examined after six days and the total number of animals killed recorded.

TABLE 4

| Bioassay Heat Treated *P. fluorescens* | | | |
|---|---|---|---|
| Treatment (70° C.) | | # Larvae Killed/Total Larvae | |
| Time (min) | # Viable Cells/Total Cells | 1× | % Killed |
| 3 | 2 × 10E5/5.5 × 10E10 | 8/8 | 100 |
| 5 | 2 × 10E6/5.5 × 10E10 | 8/8 | 100 |
| 10 | 0/5.5 × 10E10 | 8/8 | 100 |

It is evident from the above results, that the killed bacteria containing toxin provide many advantages, while still retaining all or a substantial proportion of the activity of the pesticidal activity of the live bacteria. Maintenance of dead bacteria for storage, transportation and application is more convenient and economic than employing the live organisms. At the same time, the organisms provide encapsulated protection of the toxins, so as to maintain the toxins' bioactivity for long periods of time. In addition, denaturation of the proteases prevents proteolytic degradation of the polypeptide pesticides. Various means for killing the organisms without disrupting their structure or denaturing the protein pesticide can be employed to provide the desired pesticidal activity, while providing for a convenient pesticidal composition for use in formulation and application to plants and plant products.

Although the foregoing invention has been described in some detail by way of illustration and example for purposes of clarity of understanding, it will be obvious that certain changes and modifications may be practiced within the scope of the appended claims.

We claim:

1. A pesticidal composition comprising pesticide-containing substantially intact microbial cells and an inert carrier wherein:

(1) the microbial cells have been stabilized with a chemical reagent selected from the group consisting of halogenating agents, aldehydes, anti-infective, alcohols and histological fixatives under conditions such that the cells have prolonged pesticidal activity when applied to the environment of a target pest; and (2) the pesticide is a polypeptide, which remains intracellular after stabilisation, and is produced as a result of expression of a heterologous gene in the microbial cell, and which pesticide becomes accessible to a target pest upon ingestion of the cell by a pest.

2. A pesticidal composition, according to claim 1, wherein said cells are prokaryotes or lower eukaryotes.

3. A pesticidal composition, according to claim 2, wherein said prokaryote cells are selected from the group consisting of Enterobacteriaceae, Bacillaceae, Rhizobiaceae, Spirillaceae, Lactobacillaceae, Pseudomonadaceae, Azotobacteraceae, and Nitrobacteraceae.

4. A pesticidal composition, according to claim 2, wherein said lower eukaryotic cells are selected from the group consisting of Phycomycetes, Ascomycetes, and Basidiomycetes.

5. A pesticidal composition, according to claim 1, wherein said cells are a pigmented bacteria, yeasts, or fungi.

6. A pesticidal composition, according to claim 1, wherein said microbial cells are Pseudomanas.

7. A pesticidal composition, according to claim 1, wherein said substantially intact microbial cells are stabilized with formalin.

8. A pesticidal composition, according to claim 1, wherein said substantially intact microbial cells are stabilized with iodine.

9. A pesticidal composition, according to claim 1, wherein said microbial cells are is Pseudomonas and said toxin is a *B. thuringiensis* toxin.

10. A pesticidal composition, according to claim 1, wherein said pesticide polypeptide is a *Bacillus thuringiensis* pesticide toxin.

11. A method of protecting a host susceptible to an invertebrate pest which comprises applying to the environment of the pest an effective amount of a pesticidal composition which comprises pesticide-containing substantially intact microbial cells wherein:

(1) the microbial cells have been stabilized with a chemical reagent selected from the group consisting of halogenating agents, aldehydes, anti-infectives, alcohols and histological fixatives under conditions such that the cells have prolonged pesticidal activity when applied to the environment of a target pest; and (2) the pesticide is a polypeptide, which remains intracellular after stabilisation, and is produced as a result of expression of a heterologous gene in the microbial cell, and which pesticide becomes accessible to the target pest upon ingestion of the cell by a pest.

12. A method, according to claim 11, wherein said microbial cells are prokaryotes or lower eukaryotes.

13. A method according to claim 12, wherein said prokaryotic cells are selected from the group consisting of Enterobacteriaceae, Bacillaceae, Rhizobiaceae, Spirillaceae, Lactobacillaceae, Pseudomonadaceae, Azotobacteraceae, and Nitrobacteraceae.

14. A method, according to claim 12, wherein said lower eukaryote microorganisms are selected from the group consisting of Phycomycetes, Ascomycetes, and Basidiomycetes.

15. A method according to claim 11, wherein said microbial cells are pigmented bacteria, yeasts, or fungi and said pesticide is an insecticidal polypeptide.

16. A method, according to claim 11, wherein said microbial cells are stabilized by treatment with formalin.

17. A method, according to claim 11, wherein said microbial cells are stabilized by treatment with iodine.

18. A method, according to claim 11, wherein said host susceptible to an invertebrate pest is a plant.

19. A method, according to claim 11, wherein said pesticide polypeptide is a *Bacillus thuringiensis* pesticide toxin.

* * * * *

UNITED STATES PATENT AND TRADEMARK OFFICE
CERTIFICATE OF CORRECTION

PATENT NO. : 4,695,455

DATED : September 22, 1987

INVENTOR(S) : Andrew C. Barnes and Susan G. Cummings

It is certified that error appears in the above-identified patent and that said Letters Patent are hereby corrected as shown below:

Col. 4: line 3: "ity" should read --ity;--; line 4: "toxin" should read --toxin;--; line 8: "Rhodotorula" should be italicized; "Aureobasidium" should be italicized; line 8-9: "Saccharomyces" should be italicized; line 9: "Sporobolomyces" should be italicized; line 10: "Pseudomonas" should be italicized; "Erwinia" should be italicized; line 10-11: "Flavobacterium" should be italicized; line 15: "Escherichia coli" should be italicized; "Bacillus subtilus" should be italicized; line 32: "quaternaries" should read --quaternaries;--; line 33: "amidines" should read --amidines;--; line 37: "oxide" should read --oxide;--.

Col. 6: line 22: "hyde" should read --hyde;--; line 23: "chloride" should read --chloride;--; line 24: "ethanol" should read --ethanol;--.

Col. 7: line 37: "pSM-117" should read --pSM1-17--; line 42: "pSM-117" should read --pSM1-17--; line 51: "pSM-117" should read --pSM1-17--.

Col. 8: line 9: "(pSM-117)" should read --(pSM1-17)--.

Cla. 6: line 2: "Pseudomana" should read --Psuedomonas--.

Cla. 9: line 2: "cel" should read --cells are--.

Signed and Sealed this

Sixteenth Day of February, 1988

Attest:

DONALD J. QUIGG

Attesting Officer

Commissioner of Patents and Trademarks